United States Patent [19]

Nemeth et al.

[11] Patent Number: 5,233,097
[45] Date of Patent: Aug. 3, 1993

[54] OXIDATION OF AROMATICS TO HYDROXYAROMATICS USING ALUMINOSILICATES CONTAINING FRAMEWORK TITANIUM

[75] Inventors: Laszlo T. Nemeth, Palatine; Eric M. Hyatt, Naperville; Thomas P. Malloy, Lake Zurich, all of Ill.

[73] Assignee: UOP, Des Plaines, Ill.

[21] Appl. No.: 961,300

[22] Filed: Oct. 15, 1992

[51] Int. Cl.$^5$ .................. C07C 37/60; C07C 41/26
[52] U.S. Cl. .................. 568/803; 568/629; 568/650; 568/735; 568/741; 568/743; 568/763; 568/771
[58] Field of Search .............. 568/629, 631, 648, 650, 568/735, 741, 743, 763, 771, 803

[56] References Cited

U.S. PATENT DOCUMENTS

| | | | |
|---|---|---|---|
| 3,531,519 | 9/1970 | Parkin et al. | 568/803 |
| 3,662,006 | 5/1972 | Massie et al. | 568/803 |
| 4,396,783 | 8/1983 | Esposito et al. | 568/706 |
| 4,410,501 | 10/1983 | Taramasso et al. | 423/326 |
| 5,098,687 | 3/1992 | Skeels et al. | 423/118 |

FOREIGN PATENT DOCUMENTS 2116974 10/1983 United Kingdom ............ 568/803

OTHER PUBLICATIONS

La Chimica and L'Industria, 72–1990, pp. 610–616.
A. Thangaraj et al., *J. Applied Catalysis*, 57, (1990), L1–L3.
*Structure–Activity and Selectivity Relationships in Heterogeneous Catalysis*, R. K. Grasselli and A. W. Sleight, Editors, 1991, Elsevier Science Publishers B.V., Amsterdam.
*J. Molec. Catalysis*, 68, (1991), 45–52.
Reddy and Kumar, *Jour. of Catalysis*, 130, 440–6 (1991).

*Primary Examiner*—Werren B. Lone
*Attorney, Agent, or Firm*—Thomas K. McBride; Eugene I. Snyder

[57] ABSTRACT

Certain crystalline titanoaluminosilicate molecular sieve compositions having titanium, aluminum, and silicon present as framework tetrahedral oxide units are particularly effective in hydroxylating the aromatic nucleus of aromatic compounds using hydrogen peroxide, even where the hydrogen peroxide is used at concentrations of 10 weight percent or less. The variant where the exchangeable hydrogens of the titanoaluminosilicate are replaced by an alkali or alkaline earth metal cation is particularly favored because of the concomitant increase in selectivity. Excellent utilization of hydrogen peroxide often is observed, even when the hydroxylation is effected at temperatures under about 60° C.

16 Claims, No Drawings

OXIDATION OF AROMATICS TO HYDROXYAROMATICS USING ALUMINOSILICATES CONTAINING FRAMEWORK TITANIUM

BACKGROUND OF THE INVENTION

One of the most challenging and formidable tasks in preparative organic chemistry is the selective functionalization of a carbon-hydrogen bond. Once a functional group has been introduced onto a carbon, the chemist has a rich selection of tools to achieve further transformations and transpositions, but it is clear that the initial barrier of introducing a functional group is determinative of further chemistry.

It is not only necessary that a given functionalization reaction proceed in good yield, but it also is necessary that it proceeds with specificity. Consider, for example, the reaction of simple hydrocarbons with oxygen which has multiple reaction paths including,

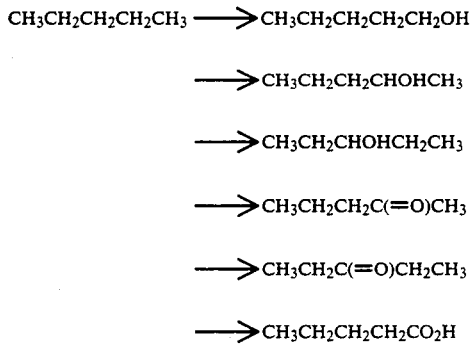

as well as numerous other products arising from carbon-carbon bond cleavage. It is clear that it will be only the rare case where such indiscriminate oxidation will be a useful process for functionalization of a carbon-hydrogen bond.

Thus recent disclosures that certain titanium-containing molecular sieves are reasonably selective and active in the oxidation of an aromatic to a hydroxy-aromatic compound according to the equation,

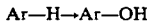

where Ar is an aromatic moiety, are particularly noteworthy. We now proceed to briefly review this art not only to determine its precise content but also to clearly distinguish our invention from the prior art teachings.

In U.S. Pat. No. 4,396,783 the patentees disclosed the oxidation of phenols to hydroquinone and pyrocatechol by hydrogen peroxide at 80°–120° C. as catalyzed by a crystalline silica (silicalite) modified by introduction into the molecular sieve of a metal such as chromium, beryllium, titanium, vanadium, manganese, iron, cobalt, zinc, zirconium, rhodium, silver, tin, antimony, and boron. The reaction can be heterogeneous or it can be conducted in the presence of the solvent such as water, methanol, acetone, isopropyl alcohol, and acetonitrile, all of which provide at least partial miscibility with hydrogen peroxide. The patentees also reported that in addition to phenols the reaction proceeded on substrates such as toluene, anisole, xylenes, mesitylene, benzene, nitrobenzene and ethylbenzene. Although the yield of hydroxylated products from phenol and anisole are on the order of 50%, no results were given for benzene. It is significant that the yields for the hydroxylation of toluene generally were about 20%, although there were two examples where the yield was approximately 40%.

Taramasso et al. in U.S. Pat. No. 4,410,501 describe titanium silicalites (TS-1) where the atom ratio of titanium to silicon was in the range of 0.0005–0.04, and in GB 2,116,974 they described their use in the oxidation of phenols to diphenols. Where the oxidation was done at a high molar ratio of phenol to hydrogen peroxide (i.e., a large excess of phenol) and at 80°–120° C., the utilization of hydrogen peroxide (given by the patentees as "H$_2$O$_2$ yield") was high, approaching 90%, but as the mole ratio decreased the peroxide utilization dropped to about 60% accompanied by a decrease in phenol selectivity. The reactivity of TS-1 in catalyzing the oxidation of various organics by hydrogen peroxide was summarized in La Chimica and L'Industria, 72–1990, pages 610–616, where phenol hydroxylation to hydroquinone and catechol was reported at some length. Pertinent to the discussion here is the observation that yields based on converted hydrogen peroxide were in the order of 80% at 100% hydrogen peroxide conversion when the reaction was performed at reflux in water, in methanol, and in 60:40 water:acetone and at a peroxide:phenol molar ratio of 0.25–0.35 and the peroxide was in the form of 30% aqueous hydrogen peroxide. Thus, even with a large excess of phenol, conversions were modest.

A. Thangaraj et al., *J. Applied Catalysis*, 57, (1990), L1–L3, studied the oxidation of benzene by hydrogen peroxide to phenol and benzoquinone as catalyzed by various zeolites and molecular sieves. Of particular importance to this application is the observation that whereas the selectivity of hydrogen peroxide utilization to oxygenated aromatics decreased in the order,

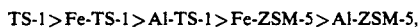

the selectivity to phenol vis a vis total oxidized benzenes increased in the same order. Stated differently, TS-1 was the most effective material in the utilization of H$_2$O$_2$ in forming oxidized benzenes, but it afforded the greatest product spectrum. What is also significant is the observation that an aluminum-containing TS-1 (Si/Al=86, Si/Ti=24) afforded only 37% selectivity in hydrogen peroxide decomposition with respect to hydroxy benzenes formation. It is particularly significant to observe that the zeolites were freed of sodium ions prior to use. Particularly relevant is the statement by Notari based on experimental data [*Structure-activity and Selectivity Relationships in Heterogeneous Catalysis*, R. K. Grasselli and A. W. Sleight, Editors, 1991, Elsevier Science Publishers B. V., Amsterdam] that the yield of hydrogen peroxide (that is, the molar percentage of hydrogen peroxide decomposition which leads to phenolic products) decreases with the addition of sodium or potassium ions to TS-1, where the magnitude of the decrease is a function of the amount of alkali metal added. For example, the addition of 7060 ppm potassium ion reduced the hydrogen peroxide yield from 79.5 to 0, and the addition of 3529 ppm sodium ion reduced the peroxide yield from 79.5 to 22.

Tuel and coworkers studied the solvent effects in phenol oxidation by hydrogen peroxide as catalyzed by TS-1 [*J. Molec. Catalysis*, 68, (1991), 45–52]. Another titanium silicalite, TS-2, with a MEL structure recently was synthesized by Reddy and Kumar, *Jour. of Cataly-* sis, 130, 440–6 (1991), who observed it to be catalytically active in the oxidation of benzene by 26% hydrogen peroxide. Although the predominant product was phenol, para-benzoquinone was produced in over 30% yield.

A fair summary of the prior art TS-1 titanium silicalite is that it is active in the oxidation of phenol at 80°–120° C., especially with a solvent in the absence of alkali metals. Benzene itself is considerably more difficult to oxidize and is oxidized far less selectively than phenol since significant amounts of benzoquinone accompany phenol formation. Incorporation of aluminum into the framework adversely effects hydrogen peroxide utilization efficiency, and a concentration of peroxide of at least 26% is necessary as an oxidizing agent. A high molar ratio of aromatic to hydrogen peroxide usually is necessary to obtain high (at least 90%) utilization of hydrogen peroxide, but decreasing the ratio generally led to a dramatic decrease in hydrogen peroxide utilization. That benzene is much less active than phenol is not surprising in view of the generally activating effect the hydroxyl group has on an aromatic ring.

Although it is promising start, the results with TS-1 are inadequate for a commercial process of oxidation of, for example, benzene to phenol. Any commercial process would require that dilute peroxides would be sufficient—something on the order of 5% hydrogen peroxide instead of the prior art's 26–30% hydrogen peroxide. A commercial process also requires that approximately equal molar amounts of benzene and hydrogen peroxide be used with high efficiency of hydrogen peroxide utilization, i.e., approximately 90%. A commercially feasible process also would require a high conversion of the aromatic, such as benzene, above about 80%, but above all one with a high selectivity to the hydroxy aromatic, e.g., phenol. We have found that certain aluminosilicates having titanium in the framework, and especially those which have been exchanged with an alkali or alkaline earth metal cation, are effective in oxidizing aromatics to hydroxyaromatics using hydrogen peroxide, especially in dilute (i.e., under 10%) solutions. It is particularly noteworthy that the prior art teaches that both incorporation of aluminum into the zeolite and the presence of an alkali metal cation are detrimental to the catalytic effectiveness of a titanium-zeolite in oxidizing aromatics by hydrogen peroxide. Accordingly, one would hardly suspect that our formula for success would be advantageous.

SUMMARY OF THE INVENTION

The purpose of this invention is to hydroxylate an aromatic compound with hydrogen peroxide, especially at moderate temperatures with good utilization of the hydrogen peroxide and good selectivity in product formation. An embodiment comprises hydroxylating the aromatic nucleus of an aromatic compound by reacting the aromatic compound with hydrogen peroxide at a temperature from about 10 to about 60° C. in the presence of a zeolite molecular sieve titano-aluminosilicate composition where the titanium, aluminum, and silicon are present as framework tetrahedral oxide units. In a more specific embodiment the hydrogen peroxide is used at a concentration not greater than about 10 weight percent. In another embodiment the zeolite molecular sieve has its exchangeable hydrogens replaced by an alkali metal or an alkaline earth metal cation. In yet another embodiment the zeolite molecular sieve is first calcined at a temperature between about 500° and 750° C. in air, nitrogen, carbon monoxide, or hydrogen. In still another embodiment the titanoaluminosilicate composition is calcined in hydrogen at 500°–750° C. Other embodiments will become apparent from the ensuing description.

DESCRIPTION OF THE INVENTION

This invention is based on the observation that however effective titanium-containing silicalites may be in catalyzing the hydroxylation of an aromatic compound by hydrogen peroxide, the members of a class of titanoaluminosilicate zeolite molecular sieves are far more effective as catalysts. The catalytic effectiveness is evidenced by the fact that hydroxylation may be effected in many instances using approximately equal molar amounts of hydrogen peroxide and the aromatic compound with high, sometimes virtually quantitative, utilization of the hydrogen peroxide. Their effectiveness also may be evidenced by the fact that concentrated hydrogen peroxide solutions, i.e., 26–30% aqueous hydrogen peroxide, need not be used in the practice of the invention in order to effect hydroxylation in good yield and with good selectivity, but that good results can be obtained even with dilute hydrogen peroxide solutions, that is, solutions under about 10 weight percent peroxide and usually on the order of 5%. The greater effectiveness is also evidenced by the fact that hydroxylations are routinely performed at temperatures in the 10°–60° C. range, which is substantially lower than that required for the titanium-containing silicalites.

A wide range of aromatic compounds may be hydroxylated in the practice of this invention with the limitation in the aromatic compound arising more from the structural characteristics of the molecular sieve used than from the chemical characteristics of the aromatic compound. The catalysts used in the practice of this invention are crystalline titanoaluminosilicate zeolites having a three-dimensional framework with $Si^{4+}$, $Ti^{4+}$ and $Al^{3+}$ in tetrahedral coordination with 4 oxygens, and where all of the oxygens in the tetrahedra are mutually shared between the tetrahedral silicon, titanium, or aluminum atoms. The assemblage of linked tetrahedral units leads to discrete channels with a well-defined size and shape within the crystalline material arising from secondary building units, i.e., the framework topology. It is the channels within the crystalline, microporous titanoaluminosilicate catalysts of our invention which place limitations on the aromatic compound which can be used. In particular, in order to be hydroxylated the aromatic compound should be capable of entering the channels of the microporous crystalline molecular sieves used as our catalysts. Since both the size and shape of the channels will vary with a particular molecular sieve used, it is clear that the particular aromatic compounds which can be hydroxylated also will vary with the molecular sieve used as the catalyst. However, since the channel size and shape of each molecular sieve are reasonably well known to those skilled in the art, it will require little or no experimentation to determine which aromatic compound may be used with a particular molecular sieve. In general, benzene, monosubstituted benzenes, biphenyl, diphenylether, alpha, omega-disubstituted linear alkanes, and even naphthalenes may be used. With increasing size of the channels in the molecular sieves, disubstituted benzenes, mono- and disubstituted biphenyls, substituted diphenylethers, and so on, may be used in the practice of this invention. It needs to be emphasized that the limitations as to the aromatic compound are the channel size and shape; if the aromatic compound sits in the channel it can be used as a substrate.

The primary oxidizing agent which is used in the practice of this invention is hydrogen peroxide, especially as aqueous solutions. Thirty weight percent solutions of hydrogen peroxide in water have been the standard in the prior art, but their disadvantage is that of cost. One important advantage of the catalysts of our invention is that they are effective in bringing about hydroxylation even with dilute—i.e., under about 10%—aqueous hydrogen peroxide as the oxidizing agent. Thus, we have used 5% aqueous hydrogen peroxide solutions to convert benzene to phenol in virtually quantitative yields and with virtually 100% efficiency in utilization of hydrogen peroxide. As to the relative amounts of hydrogen peroxide and aromatic compound, we have found that a high efficiency of peroxide utilization can be achieved using even approximately equal molar amounts of hydrogen peroxide and the aromatic compound. In the most usual case, from about 0.9 to about 1.1 molar proportions of hydrogen peroxide are used per mole of aromatic compound. However, where one component is much more expensive than the other, the molar proportions of hydrogen peroxide to aromatic compound may vary between 0.5 and 2.0, or even between about 0.2 and about 5. But we emphasize that because of the excellent efficiency in utilization of hydrogen peroxide by the catalysts of our invention, it is feasible to use approximately equal molar proportions of the two reactants.

Although hydrogen peroxide is by far the most preferable peroxide to use in the practice of this invention, other peroxides also may be used in appropriate circumstances. For example, if a completely homogeneous reaction mixture is required without the use of a solvent then an organic peroxide may be used instead of hydrogen peroxide. Examples of organic peroxides which are suitable include peroxycarboxylic acids, $RCO_3H$, alkyl hydroperoxides, $ROOH$, and dialkyperoxides, $ROOR$. Illustrative members of the aforementioned class include peroxyacetic acid, peroxybenzoic acid, peroxyformic acid, t-butyl hydroperoxide, and di-t-butylperoxide. Among inorganic peroxides which may be used peroxydisulfuric acid is the most common representative.

The molecular sieve compositions used as catalysts in the practice of our invention are largely those described by Skeels et al. in U.S. Pat. No. 5,098,687, all of which is hereby incorporated by reference. In particular, the crystalline molecular sieve compositions are those having a three-dimensional microporous framework structure of $AlO_2$, $SiO_2$ and $TiO_2$ tetrahedral oxide units with a unit empirical formula on an anhydrous basis of $(Ti_xAl_ySi_z)O_2$, where y represents the atom fraction of aluminum in the framework and is at least 0.02, where x represents the atom fraction of titanium in the framework and is at least 0.02, and where z represents the atom fraction of silicon in the framework and is at least 0.5. More typically, the value of each of x and y will be between about 0.02 and about 0.48, z will range from 0.50 to 0.96, and $x+y+z=1.0$.

Representatives of the crystalline aluminosilicate zeolite molecular sieves which may be employed to afford the titanoaluminosilicate catalysts of this invention include, but are not limited to, erionite, mordenite, clinoptilolite, zeolite Y, zeolite L, zeolite LZ-105, zeolite omega, zeolite beta, zeolite TMA offretite, zeolite ZSM-5, zeolite ZSM-34, zeolite ZSM-35, and zeolite LZ-202. Both naturally occurring and synthetically prepared zeolite molecular sieves can be used. Zeolite Y is disclosed in U.S. Pat. No. 3,130,007; zeolite L is disclosed in U.S. Pat. No. 3,216,789; zeolite LZ-105 is disclosed in U.S. Pat. No. 4,257,885; zeolite omega is disclosed in U.S. Pat. No. 4,241,036; zeolite beta is disclosed in U.S. Pat. No. 3,308,069; zeolite ZSM-5 is disclosed in U.S. Pat. No. 3,702,886; and ZSM-34 is disclosed in U.S. Pat. No. 4,086,186; and zeolite ZSM-35 is disclosed in U.S. Pat. No. 3,992,466. Examples of the titanoaluminosilicate molecular sieves include those molecular sieves having the crystal structure selected from the group consisting of erionite, mordenite, clinoptilite; zeolite Y, zeolite $\Omega$, zeolite $\beta$, zeolite TMA offretite, zeolite ZSM-5, zeolite ZSM-34, zeolite ZSM-35, zeolite LZ-202, and zeolite LZ-105. Particularly favored in the practice of our invention are the titanium aluminosilicates based on LZ-105 and ZSM-5.

It has been observed that for many of the titanoaluminosilicate catalysts of our invention a particularly desirable variant is one where the molecular sieve has its exchangeable hydrogen ions replaced by one of the alkali metal or alkaline earth metal cations. It appears that alkali/alkaline earth metal exchange invariably increases selectivity but not necessarily conversion of the aromatic compound to the hydroxylated aromatic compound. Examples of cations which can be used to exchange the hydrogen include lithium, sodium, potassium, and cesium monocations and the dications of calcium, magnesium, beryllium, strontium, and barium. The variant where the exchangeable hydrogen ions are replaced by an alkali metal cation, especially sodium or potassium, and preferably potassium, is particularly favored. The amount of alkali/alkaline earth metal exchanged is desirably sufficient to neutralize all the potential acid sites in the zeolite, which corresponds to the aluminum present in the titanoaluminosilicate. If the alkali/alkaline earth metal is designated as M, then the ratio $M/Al=1$ corresponds to complete neutralization of the acid sites and is the optimum amount of metal to be incorporated by exchange. Thus it is readily seen that the optimum alkali/alkaline earth metal content varies with the aluminum content of the titanoaluminosilicate.

Another variant which has been found effective in increasing both the activity and selectivity of the molecular sieve used as an hydroxylation catalyst is the calcination of the sieve at a temperature between about 500° and about 750° C. Calcinations may be performed in air, nitrogen, carbon monoxide, or hydrogen, and it has been observed consistently that calcination in hydrogen affords a better catalyst than when calcination is performed at the same temperature in air, nitrogen, or carbon monoxide.

It also has been found that the use of solvents to increase miscibility and to provide at least microhomogeneity with respect to hydrogen peroxide and the aromatic compound has an important beneficial effect. Thus, the use of such solvents as alcohols, ketones, carboxylic acids, nitriles, and, in some cases, even water has been found to be beneficial. The purpose of the solvent is to solubilize, at least in part, both the aromatic compound and hydrogen peroxide, and so long as the solvent accomplishes this without significantly decreasing the utilization efficiency of hydrogen peroxide and without being itself involved in a chemical reaction its nature is unimportant. Thus, methanol, ethanol, isopropyl alcohol, acetone, methyl ethyl ketone, acetic acid, and acetonitrile have been used with advantage as solvents in our invention. More generally, alcohols and ketones from 1–4 carbon atoms, nitriles with up to 5 carbons, and carboxylic acids having up to about 6 atoms will suffice.

The effect of solvents is to promote better contact between the aromatic compound and hydrogen peroxide, thus the use of solvents in which both the aromatic and hydrogen peroxide are at least partially soluble. Another means of promoting such contact is to use a phase transfer agent to effect the transfer of hydrogen peroxide into the phase with the aromatic compound, or the transfer of the aromatic compound into the aqueous phase of hydrogen peroxide. Yet another means of achieving the same result to conduct the reaction in the presence of a surfactant which in effect acts as a phase transfer agent by forming emulsions or microemulsions.

Our method may be practiced either in a batch or in a continuous mode. For example, where a batch reaction is performed catalyst is used in an amount anywhere from about 5 up to perhaps 40 weight percent based on the aromatic substrate to be hydroxylated, although even larger amounts of catalyst may be employed but not necessarily with a corresponding incremental increase in reaction rate. Reaction times of 24 hours generally suffice, especially where a solvent such as acetone is used, with an approximately equal molar proportion of hydrogen peroxide and the aromatic substrate. The hydrogen peroxide may be present as an aqueous solution of even 5% hydrogen peroxide, although more concentrated solutions of course may be used. Reaction temperatures are between 10° and 60° C., preferably at as low a temperature within this range as is consistent with an acceptable reaction rate.

Our hydroxylation also may be effected in a continuous mode by passing a mixture of the reactants over a fixed bed of the titanoaluminosilicate used as the hydroxylation catalyst. The use of a homogeneous feedstock is advantageous in ensuring adequate contact between the hydrogen peroxide and the aromatic substrate in a fixed bed operation. Failing a completely homogeneous reaction mixture, it is important that sufficient aromatic compound and hydrogen peroxide be present in at least one of the phases to ensure adequate conversion of the aromatic compound. Reaction temperatures between 10° and 60° C. are once again employed, and the reaction mixture usually contains approximately equal molar proportions of hydrogen peroxide and aromatic substrates.

A variant which is advantageous is the batch recycle mode of reaction. In this variant the reaction mixture of aromatic compound, hydrogen peroxide, and solvent, phase transfer agent or surfactant where used, is passed to a reaction zone where it flows over a fixed bed of catalyst to afford partial hydroxylation of the aromatic compound. The product is then recycled to the reaction zone and once more flowed through the fixed-bed of the catalyst. In this way, virtually quantitative yields of hydroxylated aromatic compound may be attained, as for example in the conversion of benzene to phenol, even with only equal molar amounts of hydrogen peroxide.

The following examples merely illustrate this invention and are not intended to limit it in any way.

EXAMPLE 1

Preparation of Titanoaluminosilicates

These materials were prepared generally as described in U.S. Pat. No. 5,098,687. The titanosilicalite TS-1 was prepared as described in the literature. The following detailed descriptions for the preparation of Ti LZ-105 and Ti ZSM-5 are representative of the procedures followed.

Preparation of Titanium Substituted LZ-105: (Ti LZ-105)

Ammonium exchanged LZ-105, 500 g on an anhydrous basis, was added to 5 l deionized water in a 12 l round bottomed flask and heated to 70° C. $(NH_4)_2TiF_6$, 78.8 gm, was added to the zeolite slurry in increments; 26.3 gm initially, 26.3 gm after 10 minutes, and 26.3 gm after 20 minutes. After the final addition of the fluorotitanate salt, the slurry was heated to 95° C. and held for 66 hours. The slurry was filtered hot and washed well with hot deionized water until the filtrate tested negative for residual fluoride by addition of $CaCl_2$ to the filtrate. The following analytical data were obtained on the Ti LZ-105 sample and are compared to the starting LZ-105.

| | LZ-105 | Ti LZ-105 |
|---|---|---|
| $Na_2O$, wt. %: | 0.02 | 0.02 |
| $(NH_4)_2O$, wt. %: | 2.02 | 1.43 |
| $Al_2O_3$, wt. %: | 4.45 | 3.77 |
| $SiO_2$, wt. %: | 93.45 | 88.12 |
| $TiO_2$, wt. %: | 0.00 | 6.42 |
| $F_2$, wt. %: | 0.00 | 0.24 |
| $SiO_2/Al_2O_3$: | 35.67 | 39.64 |
| Cation Equivalent, $M^+/Al$: | 0.89 | 0.76 |
| Relative X-ray Crystallinity | 100% | 77% |
| McBain Adsorption Values: | | |
| $O_2$ at 100 torr, 90K; wt. %: | 17.2 | 16.2 |
| $H_2O$ at 4.6 torr, 25° C.; wt. %: | 8.8 | 7.7 |
| Framework Infrared Region: | | |
| Asymmetric Stretch, $cm^{-1}$: | 1102 | 1100 |
| Symmetric Stretch, $cm^{-1}$: | 795 | 795 |

The formulas, as $TO_2$, calculated for $NH_4$-LZ-105 and Ti LZ-105 were $(Al_{0.053}Si_{0.915})O_2$ and $(Ti_{0.050}Al_{0.046}Si_{0.905})O_2$, respectively.

Preparation of Titanium Substituted ZSM-5; (Ti ZSM-5)

Ammonium exchanged ZSM-5, 100 g on an anhydrous basis, was added into 4 separate, 1 liter 3-necked round-bottomed flasks containing 400 mL deionized water and heated to 70° C. To the samples, labeled A, B, C, and D, was added $(NH_4)_2TiF_6$ at once in the following increments: 2.01 gm into sample A; 10.04 gm into sample B; 20.08 gm into sample C; and 41.22 gm into sample D. The amounts of $(NH_4)_2TiF_6$ corresponded to 10%, 50%, 100% and 200% of the molar amount of aluminum contained in the $NH_4$-ZSM-5 samples, respectively. After the addition of the fluorotitanate salt to each sample, the slurries were heated to 95° C. and held for 24 hours. The slurries were filtered hot and washed well with hot deionized water until the filtrate tested negative for residual fluoride by addition of $CaCl_2$ to the filtrate. The following analytical data (on an anhydrous basis) were obtained on the Ti ZSM-5 samples and are compared to the starting $NH_4$-ZSM-5.

| Sample | ZSM-5 | A | B | C | D |
|---|---|---|---|---|---|
| Na$_2$O, wt. %: | 0.00 | 0.00 | 0.00 | 0.00 | 0.00 |
| (NH$_4$)$_2$O, wt. %: | 1.99 | 2.01 | 1.63 | 1.55 | 1.55 |
| Al$_2$O$_3$, wt. %: | 4.45 | 4.32 | 3.90 | 3.73 | 3.67 |
| SiO$_2$, wt. % | 93.40 | 91.59 | 89.46 | 87.43 | 87.69 |
| TiO$_2$, wt. %: | 0.00 | 0.69 | 3.80 | 6.79 | 7.30 |
| F$_2$, wt. %: | 0.00 | 0.01 | 0.07 | 0.15 | 0.12 |
| SiO$_2$/Al$_2$O$_3$: | 35.66 | 35.96 | 38.88 | 39.87 | 40.54 |
| Cation Equivalent, M$^+$/Al: | 0.87 | 0.91 | 0.82 | 0.82 | 0.83 |
| Relative X-Ray Crystallinity: | 100% | 81% | 74% | 64% | 67% |
| McBain Adsorption Values: | | | | | |
| O$_2$ at 100 torr, 90K, wt. %: | 17.4 | 16.2 | 16.4 | 16.6 | 16.1 |
| H$_2$O at 4.6 torr, 25° C.; wt. % | 9.4 | 7.7 | 8.4 | 7.8 | 7.6 |
| Framework Infrared Region: | | | | | |
| Asymmetric Stretch, cm$^{-1}$: | 1094 | 1095 | 1095 | 1095 | 1095 |
| Symmetric Stretch, cm$^{-1}$ | 795 | 795 | 796 | 796 | 796 |

The following TO$_2$ formulae were calculated: ZSM-5 (Al$_{0.053}$Si$_{0.947}$)O$_2$; A, (Ti$_{0.005}$Al$_{0.052}$Si$_{0.942}$)O$_2$; B, (Ti$_{0.029}$Al$_{0.047}$Si$_{0.923}$)O$_2$; C, (Ti$_{0.053}$Al$_{0.045}$Si$_{0.902}$)O$_2$; D, (Ti$_{0.056}$Al$_{0.044}$Si$_{0.899}$)O$_2$.

Potassium Exchange of Titanium Substituted ZSM-5

Samples A, B, C, and D were exchanged three times at reflux with excess KCl salt solution to remove all acidic properties of the zeolite. The potassium exchanged samples are labeled E, F, G, and H respectively. The analyses of the K$^+$-exchanged materials on an anhydrous basis follow.

| Sample | E | F | G | H |
|---|---|---|---|---|
| K$_2$O, wt. %: | 3.90 | 3.46 | 3.16 | 3.11 |
| (NH$_4$)$_2$O, wt. %: | 0.00 | 0.00 | 0.00 | 0.00 |
| Al$_2$O$_3$, wt. %: | 4.44 | 3.87 | 3.68 | 3.57 |
| SiO$_2$, wt. % | 90.23 | 88.83 | 85.85 | 85.45 |
| TiO$_2$, wt. % | 0.77 | 3.71 | 6.82 | 7.25 |
| F$_2$, wt. %: | 0.00 | 0.00 | 0.00 | 0.00 |
| SiO$_2$/Al$_2$O$_3$: | 34.52 | 38.91 | 39.58 | 40.63 |
| Cation Equivalent, M$^+$/Al: | 0.95 | 0.97 | 0.93 | 0.94 |
| Relative X-Ray Crystallinity: | 67% | 63% | 54% | 53% |
| McBain Adsorption Values: | | | | |
| O$_2$ at 100 torr, 90K, wt. %: | 15.5 | 15.2 | 14.7 | 14.8 |
| H$_2$O at 4.6 torr, 25° C.; wt. % | 6.9 | 6.5 | 6.2 | 6.4 |
| Framework Infrared Region: | | | | |
| Asymmetric Stretch, cm$^{-1}$: | 1096 | 1095 | 1096 | 1096 |
| Symmetric Stretch, cm$^{-1}$ | 795 | 795 | 795 | 795 |

The following TO$_2$ formulae were calculated: E, (Ti$_{0.006}$Al$_{0.054}$Si$_{0.939}$)O$_2$; F, (Ti$_{0.029}$Al$_{0.047}$Si$_{0.924}$)O$_2$; G, (Ti$_{0.054}$Al$_{0.046}$Si$_{0.901}$)O$_2$; H, (Ti$_{0.057}$Al$_{0.044}$Si$_{0.898}$)O$_2$.

Preparation of Titanium Aluminum Silicate, TS-1

TS-1 was synthesized according to the descriptions of Examples 8 and 2 of U.S. Pat. No. 4,410,501 issued to Taramasso et al. Example 8 illustrates the preparation of the aluminum containing TS-1 by using Example 2, an aluminum free synthesis preparation, as reference. Titanium ethoxide, 26.55 gms, were slowly added with stirring to 414.5 mL of distilled water in a 2 l beaker on a stirrer/hotplate. As the titanium ethoxide was added to the water it hydrolyzed forming a white precipitate. This hydrolyzed titanium containing solution was cooled to 5° C. in an ice bath. 318.6 mL of 30% H$_2$O$_2$ which had been separately cooled was added to the titanium containing solution. The solution turned orange. The solution was occasionally stirred over a two hour period while the temperature was maintained at 5° C. The precipitate slowly dissolved. 474.1 mL of 22.4% tetrapropylammonium hydroxide solution (TPA-OH), precooled to 5° C. was added. The solution became yellow and was stirred for 1 hour at 5° C. The solution was effervescing the entire time.

Separately 1.04 gms NaAlO$_2$ was dissolved in 84.89 gms Ludox TM -As-40 (an ammonia stabilized colloidal silica from DuPont Inc). Dissolution was slow. The NaAlO$_2$/Ludox TM solution was added with stirring and allowed to stand at room temperature overnight. As the solution returned to room temperature the amount of effervescence increased. Some effervescence was still noticeable after 17 additional hours. The solution was heated to 78° C. and stirred at temperature for 7 hours.

The solution was then transferred to a 2 liter Parr reactor equipped with a stirrer and placed in a heating mantel where it was heated to 175° C. for a total of 10 days. After cooling, the contents were removed, the crystals were separated from the liquid, and washed thoroughly with hot distilled water.

The chemical analysis data show the following product composition of the Taramasso patent synthesis:

| | |
|---|---|
| (TPA)$_2$O, wt. % | 9.13 |
| SiO$_2$, wt. % | 79.70 |
| Al$_2$O$_3$, wt. % | 1.30 |
| TiO$_2$, wt. % | 6.03 |
| SiO$_2$/Al$_2$O$_3$ | 103.73 |

The X-ray powder pattern showed a well crystallized MFI type zeolite, i.e., ZSM-5 or silicalite. The pattern also showed several additional peaks at 25.30, 47.90 and at 54.90 due to the presence of crystalline TiO$_2$, anatase. Calculated for the TS-1 product was Al$_{0.018}$Si$_{0.929}$Ti$_{0.053}$.

A compilation of some representative analytical data for additional titanoaluminosilicates used in this study is summarized in Table 1.

TABLE 1

| | Analyses of Molecular Sieves | | | | | |
|---|---|---|---|---|---|---|
| Sample | % Ti | % Al | % Si | x$^a$ | y$^a$ | z$^a$ |
| Ti mordenite | 3.30 | 2.75 | 40.94 | 0.042 | 0.063 | 0.895 |
| Ti NH$_4$Y | 9.05 | 5.87 | 30.94 | 0.125 | 0.144 | 0.730 |
| Ti LZ-202 | 5.34 | 3.65 | 38.33 | 0.069 | 0.084 | 0.847 |
| Ti beta | 2.82 | 1.85 | 42.39 | 0.036 | 0.042 | 0.922 |
| Ti NH$_4$L | 2.10 | 8.94 | 32.20 | 0.029 | 0.218 | 0.753 |

$^a$In formula (Ti$_x$Al$_y$Si$_z$)O$_2$, x, y and z are the atom fraction of titanium, aluminum, and silicon, resp.

Prior to their use, the titanoaluminosilicates were calcined at a temperature in the range of 550° C. and in an atmosphere of hydrogen, air, nitrogen, or carbon monoxide. It was observed that calcination in hydrogen afforded the best catalyst, and the oxidation results reported below were obtained with catalysts activated in hydrogen.

EXAMPLE 2

Effect of Metal Exchange

Samples of Ti LZ-105 were exchanged with lithium, sodium, potassium, or calcium at 80° C, for 6 hours using 100 cc of a 1 molar aqueous solution of the metal chloride per 10 g of sieve to afford materials which, after activation at 550° C. in hydrogen, were used as catalysts for benzene oxidation. Oxidations were performed batchwise as follows. A solution containing 0.25 moles each of benzene, phenol, and $H_2O_2$ in 100 mL acetone was reacted at 20° C. for 24 hours in the presence of the Ti LZ-105 as catalyst, present as 40 weight percent relative to benzene. Results are summarized in the following table.

TABLE 2

| Effect of Metal Exchanged on Oxidation | | |
|---|---|---|
| Metal | % Conversion | % Selectivity |
| none | 75.6 | 83.4 |
| Li | 85.4 | 95.3 |
| Na | 76.6 | 95.5 |
| K | 92.1 | 97.0 |
| Ca | 71.3 | 94.3 |

These results show clearly that whereas the effect of metal exchange on conversion is variable, exchange invariably leads to increased selectivity.

EXAMPLE 3

Benzene Oxidation; Catalyst Survey

The oxidation of benzene by hydroperoxide in the presence of various catalysts was studied under standard conditions (ambient temperature [ca. 20° C.], 24 hours, equimolar quantities of benzene, hydrogen peroxide (30%), and phenol dissolved in acetone (50% solution), 40 weight percent catalyst based on benzene). Both unactivated catalyst and activated potassium ion-exchanged catalyst were tested. Activation was performed by flowing hydrogen over the catalyst at 550° C. for 14 hours. Results are summarized in Table 3. Total yield of phenol is the product of conversion and selectivity, i.e., percent yield=(percent conversion)×(percent selectivity)/100.

TABLE 3

| | Catalyst Effectiveness in Benzene Oxidation with Hydrogen Peroxide | | | |
|---|---|---|---|---|
| | UNACTIVATED | | POTASSIUM ION EXCHANGE and hydrogen activation | |
| CATALYST | CONVERSION | SELECTIVITY | CONVERSION | SELECTIVITY |
| Ti Mordenite | 26.45 | 80.76 | 16.48 | 86.91 |
| Ti NH4Y | 29.36 | 84.86 | 23.76 | 94.35 |
| Ti LZ-202 | 40.70 | 83.5 | 25.01 | 89.85 |
| Ti Beta | 36.89 | 82.68 | 22.42 | 88.11 |
| Ti NH4L | 60.94 | 95.39 | 39.62 | 96.80 |
| TS-1 | 35.18 | 91.70 | 21.65 | 46.5 |
| Ti LZ-210 | 12.11 | 15.00 | 3.44 | 19.00 |
| Ti ZSM-5 | | | 89.7 | 99.5 |
| Ti LZ-105 | 75.60 | 83.44 | 92.10 | 97.1 |

EXAMPLE 4

Batch Recycle Oxidation of Benzene

One hundred mL of a reaction mixture containing 14.5 weight % benzene, 6.3 weight % $H_2O_2$ (equimolar amounts of peroxide and benzene), 21 weight % water and 58.2 weight % acetone was passed over a bed of 2 g potassium-exchanged Ti LZ-105 at ambient temperature (ca. 20° C.) and pressure at such a rate that the entire mixture passed over the bed in 1 hour (cycle time). The effluent was then used as the feedstock and recycled over the catalyst bed. The effluent was analyzed as a function of the number of recycles over the bed with results reported in Table 4. What is clear is that a dilute (6.3%) hydrogen peroxide solution affords virtually quantitative conversion of benzene with high selectivity to phenol as the product.

TABLE 4

| Batch Recycle Oxidation of Benzene | | |
|---|---|---|
| CYCLES | CONVERSION [%] | SELECTIVITY [%] |
| CATALYST ACTIVATION: 550° C., air, 14 hrs | | |
| 1 | 1.51 | 16.5 |
| 15 | 5.27 | 84.0 |
| CATALYST REACTIVATION: 550° C., nitrogen, 14 hrs. | | |
| 1 | 13.41 | 63.07 |
| 8 | 23.15 | 84.4 |
| 14 | 32.04 | 86.5 |
| CATALYST REACTIVATION: 550° C., nitrogen, 14 hrs | | |
| 1 | 36.8 | 92.9 |
| 15 | 80.44 | 85.16 |
| 16 | 85.53 | 88.6 |
| 17 | 90.59 | 87.49 |
| 18 | 93.42 | 83.3 |
| 48 | 99.09 | 83.5 |

What is claimed is:

1. A method of hydroxylating the aromatic nucleus of an aromatic compound comprising reacting the aromatic compound with a peroxide at a temperature of from about 10° to about 60° C. in the presence of a crystalline titanoaluminosilicate molecular sieve composition where the titanium, aluminum, and silicon are present as framework tetrahedral oxide units having a unit empirical formula on an anhydrous basis of $(Ti_x Al_y Si_z)O_2$ where each of x and y independently has a value between about 0.02 and about 0.48, z has a value of at least 0.50 up to 0.96, and $(x+y+z)=1$.

2. The method of claim 1 where the aromatic compound is selected from the group consisting of benzene, biphenyl, diphenylether, naphthalene, and mono- and disubstituted derivatives thereof.

3. The method of claim 1 where the peroxide is selected from the group consisting of hydrogen peroxide, peroxycarboxylic acids, alkyl hydroperoxides, dialkylperoxides, and peroxydisulfuric acid.

4. The method of claim 3 where the peroxide is hydrogen peroxide.

5. The method of claim 1 where the peroxide and the aromatic compound are reacted in a solvent.

6. The method of claim 5 where the solvent is selected from the group consisting of saturated alcohols having 1 to 4 carbon atoms, saturated ketones having up to 4 carbon atoms, and saturated carboxylic acids with 2 to about 6 carbon atoms.

7. The method of claim 4 where hydrogen peroxide is used as an aqueous solution containing not more that 10 weight percent hydrogen peroxide.

8. The method of claim 7 where hydrogen peroxide is used as an aqueous solution containing not more that 5 weight percent hydrogen peroxide.

9. The method of claim 4 where hydrogen peroxide is present in from about 0.2 to about 5 molar proportions relative to the aromatic compound.

10. The method of claim 9 where hydrogen peroxide is present in the from about 0.5 to about 2 molar proportions relative to the aromatic compound.

11. The method of claim 10 where hydrogen peroxide is present in from about 0.9 to about 1.1 molar proportions relative to the aromatic compound.

12. The method of claim 1 further characterized in that the titanoaluminosilicate is calcined in hydrogen at a temperature from about 500° to about 750° C.

13. The method of claim 1 further characterized in that the exchangeable hydrogen ions of the crystalline titanoaluminosilicate molecular sieve composition are replaced by an alkali or alkaline earth metal cation.

14. The method of claim 13 where the exchangeable hydrogen ions of the crystalline titanoaluminosilicate molecular sieve composition are replaced by an alkali metal cation.

15. The method of claim 14 where the alkali metal cation is sodium or potassium.

16. The method of claim 13 where the amount of alkali or alkaline earth metal cation exchanged is sufficient to neutralize all the potential acid sites in the zeolite.

* * * * *